(12) United States Patent
Akhtar et al.

(10) Patent No.: US 11,974,930 B2
(45) Date of Patent: May 7, 2024

(54) COMPLIANT FOUR-BAR LINKAGE MECHANISM FOR A ROBOTIC FINGER

(71) Applicant: Psyonic, Inc., Champaign, IL (US)

(72) Inventors: Aadeel Akhtar, Urbana, IL (US); Timothy Bretl, Urban, IL (US); Kyung Yun Choi, Seoul (KR)

(73) Assignee: PSYONIC, Inc., Champaign, IL (US)

( * ) Notice: Subject to any disclaimer, the term of this patent is extended or adjusted under 35 U.S.C. 154(b) by 347 days.

(21) Appl. No.: 17/512,239

(22) Filed: Oct. 27, 2021

(65) Prior Publication Data

US 2022/0183862 A1    Jun. 16, 2022

Related U.S. Application Data

(63) Continuation of application No. 16/397,457, filed on Apr. 29, 2019, now Pat. No. 11,185,427.
(Continued)

(51) Int. Cl.
*A61F 2/58*     (2006.01)
*A61F 2/50*     (2006.01)
(Continued)

(52) U.S. Cl.
CPC ...... *A61F 2/586* (2013.01); *A61F 2002/5038* (2013.01); *A61F 2002/587* (2013.01);
(Continued)

(58) Field of Classification Search
CPC .. A61F 2/586; A61F 2/741; A61F 2/68; A61F 2/72; A61F 2002/5038;
(Continued)

(56) References Cited

U.S. PATENT DOCUMENTS

| 4,143,426 A | 3/1979 | Hall et al. |
| 11,399,967 B2 | 8/2022 | Cornman et al. |

(Continued)

FOREIGN PATENT DOCUMENTS

| DE | 327490 C | 10/1920 |
| GB | 2488760 A | 9/2012 |

(Continued)

OTHER PUBLICATIONS

Translation of DE327490-C (Year: 1916).

*Primary Examiner* — Matthew J Lawson
*Assistant Examiner* — Aren Patel
(74) *Attorney, Agent, or Firm* — Alpine Patents LLC; Brian Van Osdol

(57) ABSTRACT

A system and method for a compliant four-bar linkage mechanism for a robotic finger that includes: a monolithic bone structure comprised of a compliant joint region and an input link segment and a coupler link segment, wherein the input link segment and the coupler link segment are connected through the compliant joint; an output link; a ground structure; wherein the monolithic bone structure, output link, and ground structure are connected through a set of joints in a configuration of a compliant four-bar linkage mechanism which comprises: the output link on a first end and the coupler link segment connected through an output joint, the output link on a second end connected to a ground joint on the ground structure, and the monolithic bone structure connected to an input joint connected to the ground structure; and an actuation input coupled to the input joint.

20 Claims, 13 Drawing Sheets

Related U.S. Application Data

(60) Provisional application No. 62/663,820, filed on Apr. 27, 2018.

(51) Int. Cl.
*A61F 2/68* (2006.01)
*A61F 2/70* (2006.01)
*A61F 2/72* (2006.01)
*A61F 2/74* (2006.01)

(52) U.S. Cl.
CPC ......... *A61F 2/68* (2013.01); *A61F 2002/6836* (2013.01); *A61F 2002/701* (2013.01); *A61F 2002/704* (2013.01); *A61F 2/72* (2013.01); *A61F 2/741* (2021.08)

(58) Field of Classification Search
CPC ........ A61F 2002/587; A61F 2002/6836; A61F 2002/701; A61F 2002/704
See application file for complete search history.

(56) References Cited

U.S. PATENT DOCUMENTS

| | | |
|---|---|---|
| 2005/0021154 A1 | 1/2005 | Brimalm |
| 2010/0036507 A1 | 2/2010 | Gow |
| 2010/0082103 A1 | 4/2010 | Blunn et al. |
| 2011/0054636 A1 | 3/2011 | Gill |
| 2011/0160873 A1 | 6/2011 | Jaworski |
| 2013/0053984 A1 | 2/2013 | Hunter et al. |
| 2014/0277588 A1 | 9/2014 | Patt et al. |
| 2014/0277589 A1 | 9/2014 | Veatch |
| 2015/0230941 A1 | 8/2015 | Jury |
| 2016/0250015 A1 | 9/2016 | Kim et al. |
| 2017/0007424 A1 | 1/2017 | Gill |
| 2017/0020691 A1 | 1/2017 | Thompson et al. |
| 2019/0328550 A1 | 10/2019 | Akhtar et al. |
| 2020/0306059 A1 | 10/2020 | Cornman et al. |
| 2021/0085491 A1 | 3/2021 | Akhtar et al. |

FOREIGN PATENT DOCUMENTS

| | | |
|---|---|---|
| KR | 1020190023402 | 3/2019 |
| WO | 2015193856 A1 | 12/2015 |

COMPLIANT FOUR-BAR LINKAGE MECHANISM FOR A ROBOTIC FINGER

CROSS-REFERENCE TO RELATED APPLICATIONS

This Application is a Continuation Application of U.S. patent application Ser. No. 16/397,457, filed on Apr. 29, 2019, which claims the benefit of U.S. Provisional Application No. 62/663,820, filed on Apr. 27, 2018, both of which are incorporated in their entirety by this reference.

TECHNICAL FIELD

This invention relates generally to the field of prosthetic limbs, and more specifically to a new and useful system and method for four-bar linkage for a robotic finger.

BACKGROUND

Nearly as long as humans have existed, human injuries and ailments have existed that have led to loss or lack of limb. As an inventive species, humans have constantly developed tools and prostheses to cope with these lost limbs. With human advancement these prostheses have improved and become closer in capability to the original lost limb.

With the development of myoelectric prosthetic devices, prostheses have reached a new level wherein human muscle signals could be used to control motors on or within a prosthetic limb. Myoelectric prostheses have enabled construction of complex prosthetic devices that start to resemble intact limbs in functionality. Motors and actuating components can now be incorporated into appropriately sized prosthetic limbs, enabling life-like functionality.

With miniaturization and added functionality, the durability of these prostheses becomes a limiting a factor. Smaller components tend to be more delicate, requiring greater care and leading more often to breakages. This is particularly the case for robotic fingers of a prosthetic hand. Hands are used heavily, and the motion of fingers requires both small subtle movement capability and great strength. The predominant design in use today yields actuated fingers that are rigid and susceptible to breaking during normal use. In particular, the fingers of a prosthetic hand are vulnerable to lateral impact. As this is a common occurrence, prosthetic fingers can be easily broken. Additionally, fixing broken prosthetic fingers can be non-trivial and expensive.

Thus, there is a need in the actuating prostheses field to create a new and useful system and method for a compliant four-bar linkage mechanism for a robotic finger. This invention provides such a new and useful system and method.

DESCRIPTION OF THE EMBODIMENTS

The following description of the embodiments of the invention is not intended to limit the invention to these embodiments but rather to enable a person skilled in the art to make and use this invention.

1. Overview

Figure 1:
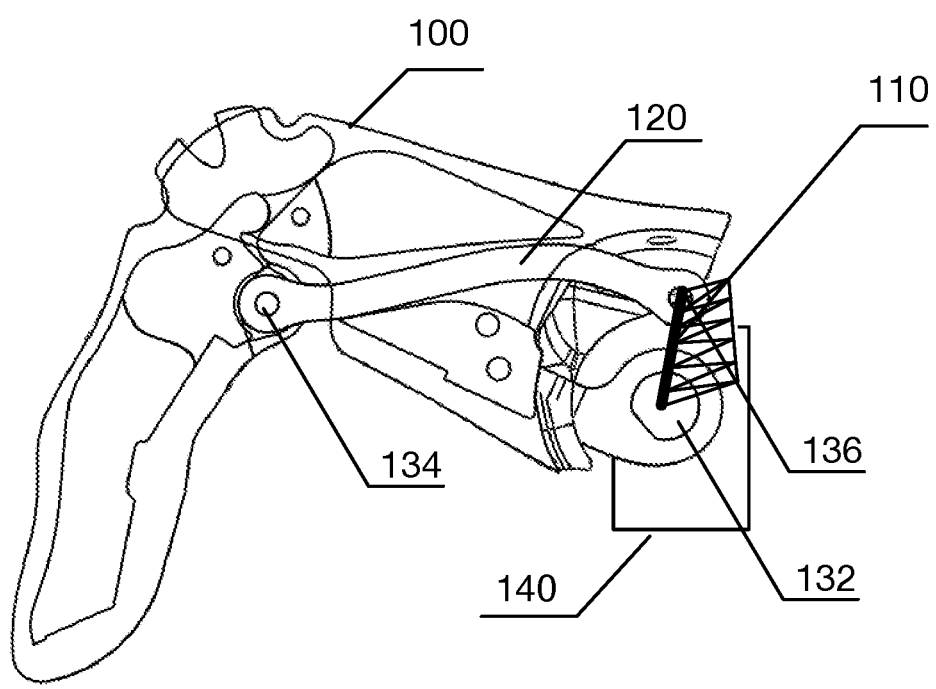
FIG. 1 is a schematic representation of a system of a preferred embodiment.

As shown in FIG. 1, a system and method for a compliant four-bar linkage mechanism of a preferred embodiment includes a compliant monolithic bone structure comprised of at least two segments integrated through a compliant joint; at least two link components; and wherein the monolithic finger bone is connected to the two link components through at least three joint components. The monolithic bone structure with its two segments and the two link components connect through the three joints. In cooperation with the compliant joint of the monolithic bone structure combine to functionally form a compliant four-bar linkage. The system and method function to make a mechanism with a range of motion comparable to a four-bar linkage mechanism that is additionally resilient to incidental forces outside of the intended range of motion.

The compliant four-bar linkage mechanism may be applied in a variety of applications where actuation is desired in a defined plane and where it is desirable to make the mechanism resilient to lateral forces.

The system and method of manufacture of the compliant four-bar linkage mechanism maybe used in a variety of use cases. One preferred use-case described herein is in the field of prosthetic devices. More specifically, the four-bar linkage mechanism may be used in creating an actuated finger of a prosthetic hand. The actuated path of the compliant four-bar linkage mechanism maintains a path of actuation suitable for simulation of finger motion. The system and method of a compliant four-bar linkage mechanism can make a finger of a prosthetic hand more impact resistant. Additionally, the system and method of a compliant four-bar linkage mechanism can be used in making four or five compliant actuating fingers: as independent fingers or as part of an actuating prosthetic hand or other device.

While the system and method are described primarily in the context of an actuated finger in a prosthesis, the system and method are not limited to this form of prosthesis. The techniques and variations of the system and method described herein may be additionally applied in other fields such as robotics, automated mechanisms, or any suitable application needing an actuating limb, lever, or mechanism.

The compliant four-bar linkage mechanism replaces both a rigid input link and a rigid coupler link of a conventional four-bar linkage with the compliant monolithic finger bone. As a prosthetic finger, the system and method may further include an outer layer functioning as an outer "skin" covering the monolithic bone. The system and method may further include a prosthetic hand, wherein a compliant four-bar linkage mechanism is included as part of one or more prosthetic fingers of the prosthetic hand. In some variations, the system and method may incorporate additional joint and link components, sensors, actuated elements, and/or other features.

The system and method may additionally incorporate mechanism design considerations that may function to enhance the manufacturability and assembly of the compliant four-bar mechanism. For example, the system and method maybe suitable for leveraging three-dimensional (3D) printing of one or more components.

As one potential benefit, the system and method may result in a four-bar linkage mechanism with enhanced impact resistance. A main site of impact failure for a traditional prosthetic hand is a pin joint between an input link and a coupler link, e.g., the proximal interphalangeal (PIP) joint of the prosthetic finger. The system and method preferably use a compliant joint, which functions to eliminate a standard pin joint. In some variations, the system and method may additionally incorporate torsional and flexural compliance in the design of a prosthetic finger. As compared to the conventional four-bar linkage, the compliant monolithic bone may bend and flex, wherein rigid components would allow for little bending or flexing. Accordingly, the compliant joint in combination with other compliance features of the system and method may enhance the impact resistance of the mechanism. As a person's hand is constantly in use, lateral impact or lateral forces are commonly encountered. Compliance of components of the system and method may allow better impact absorption that would otherwise break the prosthetic hand. Thus, compliance to such forces enhances the usability of a corresponding prosthetic.

As another potential benefit of the system and method, the compliant PIP joint may reduce energy loss due to friction from link rotation about a standard link. The reduction in parts by not needing one pin joint of a standard four-bar mechanism can eliminate a source of friction and energy loss.

As a related benefit, the mechanical design of the system and method can result in easier fabrication, assembly, and maintenance. Compliant components may allow for easier construction and assembly by enabling the use of molding or 3D printing that may not be possible with rigid components. In the case of assembly, the system and method obviate the need for one pin joint of a standard design resulting in fewer parts and fewer assembly steps. The part configuration of the system and method can similarly translate to easier disassembly (e.g., during repairs). This may make replacing finger mechanisms of a prosthetic hand easier. In terms of maintenance, the compliant joint serves as one less joint requiring maintenance like adding of lubricant.

Another potential benefit of the system and method and their use of a compliant joint maybe a reduction in hysteresis. This may translate to a more responsive prosthetic finger.

As another potential benefit, the system and method may enhance various physical attributes such as a reduction in weight, compactness of the mechanism, and an integrated structural design.

Rigid components tend to have much greater weight, and thus replacing two rigid links with a compliant monolithic bone structure may reduce the weight. The compliant monolithic finger bone may serve to reduce the weight of a prosthetic finger and thereby the prosthetic hand.

Additionally, the system and method may be used to produce small prosthetics potentially resulting from various details of the system and method such as a reduction in parts, feasibility for a molded monolithic bone structure, and/or other features. In some implementations, this maybe leveraged to create woman or child sized prostheses, where traditionally prostheses were sized larger.

Furthermore, the system and method can preferably achieve at least a portion of the benefits described herein while functionally performing at desired standards. The system and method may be used to create a prosthetic hand that may handle significant weight loads, actuate over a wide range, and suitably grasp a variety of items.

In an exemplary implementation, the system and method can result in a prosthetic hand that can hold greater than 25 kg when fully open and greater than 23 kg when the hand is grasping. Additionally, an individual finger can hold greater than a 17 kg load. Furthermore, the prosthetic could recover from loads beyond the maximum. When the applied load was larger than the maximum load the hand could hold, instead of causing mechanical damage to an actuator, a gear train or hand structure, a compliant joint (e.g., the proximal interphalangeal joint) may undergo rotational elastic deformation. The design of the prosthetic fingers may enable the fingers to recover to their initial positions and shape after exceeding the maximum load capacity. In preferred implementations, the compliance of the fingers can allow the hand to grasp various types of objects by conforming to the shape of the object. A compliant hand of the system and method may also have the benefit of being able to grip different objects using the same grasp (e.g., a power grasp) but with different final finger positions. For example, when grasping a round object, the fingertips can conform around the curved surface. When grasping a box, the fingertips can form a straight line on the flat surface of the box.

2. System

As shown in FIG. 1, a system for a compliant four-bar linkage mechanism includes a monolithic bone 100, a ground link 110, an output link 120, and a set of joints, wherein a drive joint 132 connects the monolithic bone to the ground link 110, a output joint 134 connects the monolithic bone 100 to the output link 120, and a ground joint 136 connects the ground link 110 to the output link 120. The monolithic bone 100 is preferably a compliant multi-segment structure that includes a four-bar linkage section 102.

More specifically, the system preferably includes a monolithic bone structure comprised of a compliant joint region and an input link segment and a coupler link segment, wherein the input link segment and the coupler link segment are connected through the compliant joint; an output link; and a ground structure. The monolithic bone structure, output link and ground structure are preferably connected through a set of joints in a configuration of a compliant four-bar linkage mechanism which comprises: the output link 120 on a first end and the coupler link segment connected through a output joint 134 (i.e., coupler joint), the output link 120 on a second end connected to a ground joint 110 on the ground structure, and the monolithic bone structure connected to an input joint connected to the ground structure. The system can additionally include an actuation input 140 coupled to the input joint.

When used with a hand the system may additionally include a base palm body and a set of compliant four-bar linkage mechanisms configured as prosthetic fingers. A set of actuation inputs 140 can be integrated into the base palm body. In one variation they can be worm gear actuation systems. Preferably, each four-bar linkage mechanism preferably engages with one worm gear actuation system of the set of worm gear actuation systems at an input joint of each four-bar linkage mechanism.

In the context of being applied to a prosthetic hand, the system may alternatively be described in terms of biological descriptors of the mechanical joints. Accordingly, the system may alternatively be described as a system for a prosthetic finger that includes: a monolithic bone structure comprised of a compliant proximal interphalangeal joint and an input link segment and a coupler link segment, wherein the input link segment and the coupler link segment are connected through the compliant proximal interphalangeal joint; an output link; and a prosthetic hand structure. Wherein the monolithic bone structure, output link, and a prosthetic hand structure are connected through a set of joints in a configuration of a compliant four-bar linkage mechanism which comprises: the output link on a first end and the coupler link segment connected through an output joint, the output link on a second end connected to a ground joint on the prosthetic hand structure, and the monolithic bone structure connected to a metacarpophalangeal input joint connected to the prosthetic hand structure. In some implementations the metacarpophalangeal input joint can be torsionally compliant. This variation can similarly include an actuation input coupled to the metacarpophalangeal input joint. Additionally, the monolithic bone structure may additionally include a fingertip section extending from the coupler segment. The fingertip section can include two segments connected through a compliant distal interphalangeal joint.

The compliant four bar linkage mechanism functions to provide a mechanism for planar actuation of a joint—preferably for a robotic finger. The robotic finger is preferably incorporated as part of a prosthetic hand. More specifically, the compliant four-bar linkage mechanism may function to convert an input crank motion of a motor to bending actuation of the robotic finger. The compliant four-bar linkage mechanism may alternatively be implemented for bending actuation of other artificial bodies (e.g., mechanical/robotic/prosthetic, finger, hand, arm, knee, leg, neck). In preferred variations for a robotic finger of a prosthetic hand, the compliant four-bar linkage may additionally function to increase structural integrity of the robotic finger, as compared to a rigid conventional four-bar linkage, making the prosthetic hand more impact resistant.

Figure 2A:
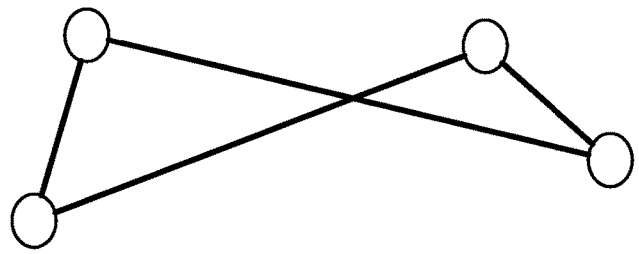
FIG. 2A is a schematic example of a four-bar linkage mechanism.
Figure 2B:
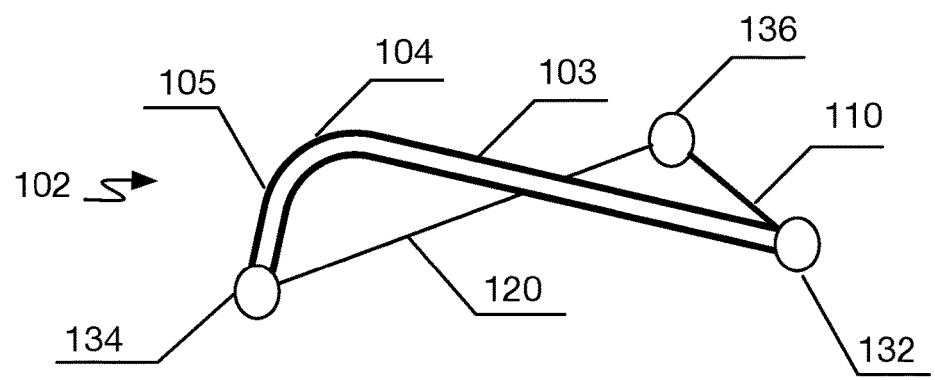
FIGS. 2B and 2C are schematic examples of compliant four-bar linkage mechanisms.
Figure 2C:
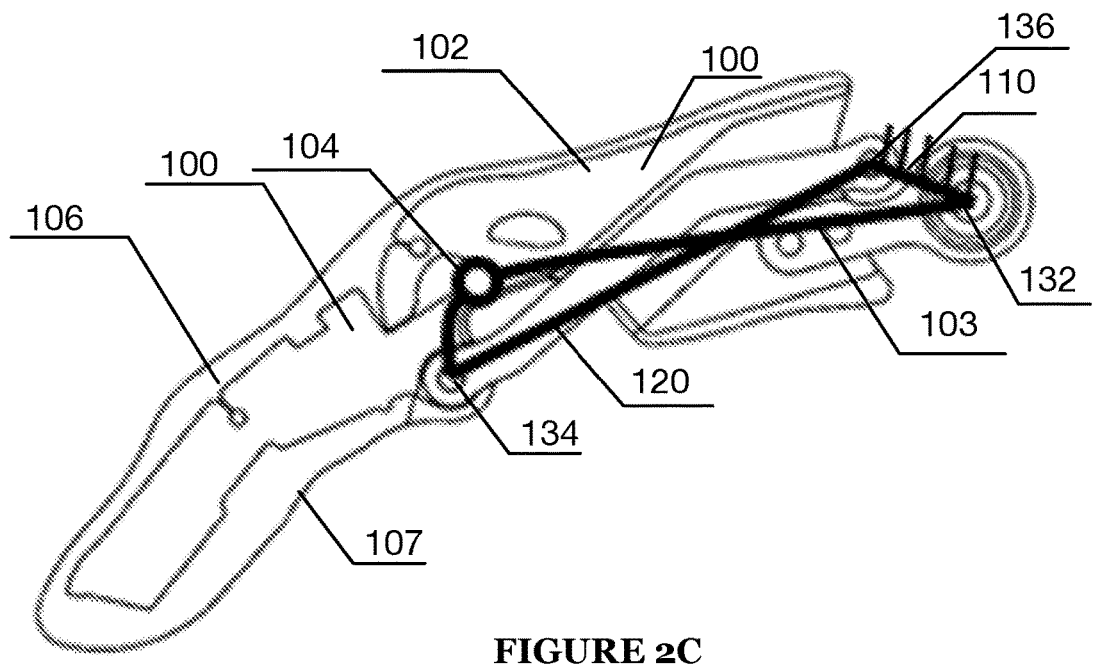

The system of a compliant four-bar linkage mechanism preferably has the functional capability of a conventional four-bar linkage. As compared to the conventional four-bar linkage, the four-bar linkage section 102 of the monolithic bone 100 may functionally replace a rigid input link, a rigid coupler link (also referred to as a floating link) and a connecting revolute joint (typically a pin joint) of the conventional four-bar linkage. Additionally, a follower link (also called output link) of the conventional four-bar linkage may be replaced with one or more layers of spring steel. The system preferably has the functionality of the conventional four-bar linkage with the added benefit of lateral compliance and elimination of a pivot joint between the input link and the coupler link of the conventional four-bar linkage (which is a major site of failure of impact for traditional prosthetic hands). As shown in FIG. 2A, a conventional four-bar linkage will traditionally include 4 revolute pin joints and 4 rigid links. As shown in FIG. 2B, the system promotes a linkage mechanism comprised of three linking structures: the ground link 110, the output link 120, and the monolithic bone 100. The monolithic bone 100, however, incorporates at least one compliant joint 104 into the structure of the monolithic bone 100. The compliant joint 104 has a flexible range such that the three linking structures actuate in a motion comparable to a four-bar linkage usable in a prosthetic finger as shown in FIG. 2C.

The monolithic bone 100 of a preferred embodiment functions as a structural support and an actuating structure as part of a four-bar linkage mechanism. The monolithic bone 100 structure is preferably a unibody component. The monolithic bone 100 may be made of a single part. Alternatively, the monolithic bone 100 may effectively act as a unibody structure but can be constructed from multiple assembled sub-components.

A proximal end of the monolithic bone 100 is preferably coupled to a ground structure. In one preferred implementation, the ground structure is preferably the base palm portion of a body of a prosthetic hand. The proximal end will preferably include a defined joint coupler. The joint coupler preferably couples with an input or driver of the mechanism, whereby a portion of the monolithic bone 100 can function as the input link of four-bar mechanism actuation. In one preferred implementation, the joint coupler mechanically engages with a worm gear driven about a revolute joint, where the worm gear is driven by a motor.

The monolithic bone 100 may additionally include a distal end that is a portion extending out from the coupler link segment of the monolithic bone 100. The distal end can be configured into the form of a fingertip and more specifically the distal phalanx of a finger. In some variations, the segment extending from the coupler link segment of the monolithic bone 100 to the distal end can include a distal interphalangeal (DIP) joint. Phrased in another way, the fingertip section can include two segments connected through a DIP joint. The DIP joint can be a compliant joint but may alternatively be an actuated joint with a controlled degree of freedom. The DIP joint may alternatively be a non-compliant, fixed position joint providing the structural presence of the distal phalanges in a prosthetic hand. Alternative applications of the monolithic bone 100 may incorporate alternative components or mechanisms into the distal end of the monolithic bone.

The monolithic bone 100 preferably includes a four-bar linkage section 102. The four-bar linkage section 102 functions as two link subcomponents and a connecting compliant joint between them. The two link subcomponents and the connecting joint are preferably compliant structures (i.e., actuating components that are not stiff rods and a rotating pivot joint). Specifically, the four-bar linkage section 102 preferably includes an input link segment 103 connected to a coupler link segment 105 through a compliant joint 104. A compliant joint 104 may be a discrete element and therefore may alternatively be characterized as a compliant joint region which is a defined sub-region of the monolithic bone 100 that functions collectively as a joint based on physical properties of the monolithic bone 100 structure. In preferred variations for the prosthetic finger, the compliant joint in this configuration may be referred to as the proximal interphalangeal (PIP) joint.

Accordingly, the monolithic bone 100 preferably includes at least two segments. A segment functions as a subsection of the monolithic bone 100 defining a region of the structure. A segment will generally characterize a structural, and at least partially, rigid section of the monolithic bone 100 extending between two points. The monolithic bone 100 will preferably include at least the input link segment 103 and the coupler link segment 105.

The monolithic bone 100 may additionally include other segments or structures, which may not be directly part of the four-bar linkage mechanism. As discussed above, the distal end of the monolithic bone 100 may include a distal segment. The distal segment may or may not include a DIP joint. Any suitable end effector or component may be integrated with the input link segment 103 and/or the coupler link segment 105.

The monolithic bone 100 preferably has a compliant flexible body structure wherein some and/or all sections of the monolithic bone 100 may bend and/or deform due to an exerted force. In one variation, the compliance of the monolithic bone 100 is centralized into localized regions, which can be referred to as a compliant joint or compliant joint region. Preferably, a compliant joint can act as a living spring with a stable "resting" position that can deform along at least one degree of freedom, and then returns to a "resting" position once the force has been removed. The degree of freedom is preferably a rotational degree of freedom. The degree of freedom may alternatively be elastic longitudinal deformation (e.g., stretching or compression) or a combination.

In some variations, a compliant joint may alternatively include multiple points of compliance or a defined region of compliance. For example, a sequence of multiple sub-regions of compliance may be integrated along a region of the monolithic bone 100. The sub-regions of compliance in combination can satisfy the motion range and resulting compliance desired to achieve the kinematic motion.

The monolithic bone preferably includes a defined form that promotes compliance in at least one localized region. In preferred variations, compliance of the monolithic bone 100 may be defined by the shape and/or composition of the section. The material thickness and structural form can be altered in different regions and along different dimensions to promote different compliance factors. A compliance factor can be a measure of stiffness, spring constant, elasticity, or any suitable metric for deformation and response under various forces. In one exemplary implementation, a joint subsection of the monolithic bone 100 may be thinner in one dimension and constructed of elastic material to allow the monolithic bone 100 to bend at the compliant joint 104 in the appropriate direction. The monolithic bone 100 preferably includes compliant sub-regions that respond differently to external forces. Different responses of the monolithic bone 100 may be due to the shape, structural makeup, method of assembly, material, and/or other suitable factors. Examples of different responses to exerted forces include: bending of the monolithic bone 100 on a finger joint subsection, in response to an exerted force on the joint in the appropriate bending direction; uniform bending of the monolithic bone 100 due to an exerted force on the finger joint in a non-bending direction; and rattling of the monolithic bone 100 due to a short impact force exerted laterally on any region of the monolithic bone 100.

As discussed, the monolithic bone 100 will preferably include at least one compliant PIP joint 104 simulating a fourth joint of a four-bar linkage. The monolithic bone 100 may additionally include a compliant DIP joint, a compliant MCP joint, and/or other compliant joints.

The compliant PIP joint may potentially have several advantages over the PIP joint of the conventional four-bar linkage including: no energy loss to friction, no requirement for lubrication, no hysteresis, easier fabrication, and a significantly reduced need for maintenance. The compliant PIP joint 104 maybe integrated into the monolithic bone 100 through a living hinge, a living spring, compliant mesh structure, compliant material region, and/or other structural solutions to structural flexibility. A living hinge variation may not have a resting position strongly enforced through mechanical properties. A living spring functions as a structural region with simulated toroidal or linear spring dynamics or in other words having a force vary linearly with deformation (linear or rotational).

A compliant mesh structure may use a combination of structural elements to promote compliance dynamics. The compliant mesh structure may comprise structural sub-components that individually act as living springs and hinges but interact based on a structural configuration that creates a resulting compliant region. Material selection and use of sub-components of select materials can be used in another variation to create controlled regions of compliance.

In some variations, the compliant PIP joint may have directionally dependent variable compliance, which can function to compensate for a variety of use-cases in a prosthesis. For example, compliance to lateral impacts should be high while compliance in the plane or direction of loading (e.g., when lifting with the fingers) may be less so that it can hold static loads. Directionally-dependent variable compliance may be implemented through construction of different spring mesh models. In one variation, the compliant joint is structurally configured with a first compliance factor within a first displacement range and a second compliance factor within a second displacement range. For example, flexing the fingers may have the joint provide a first amount of compliance, but when extending the finger beyond a set threshold a different amount of compliance is provided through the joint.

Figure 3A:
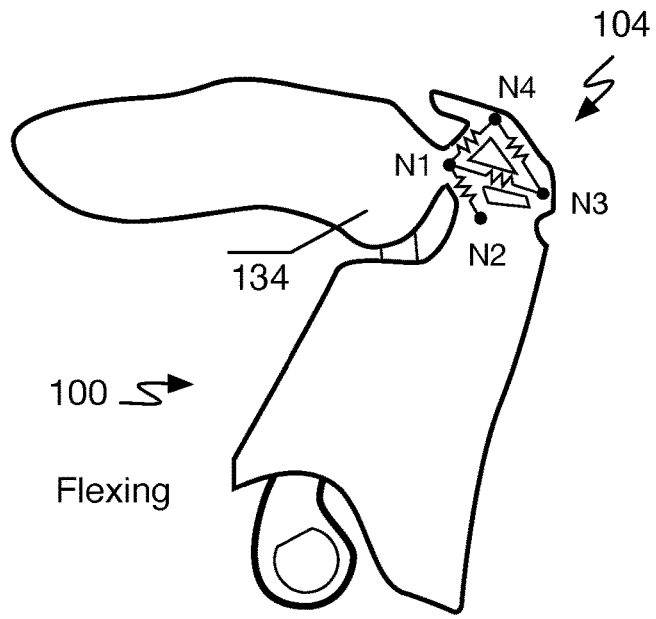
FIGS. 3A and 3B are schematic representations of a variable compliant proximal interphalangeal joint in flexing and extending states.
Figure 3B:
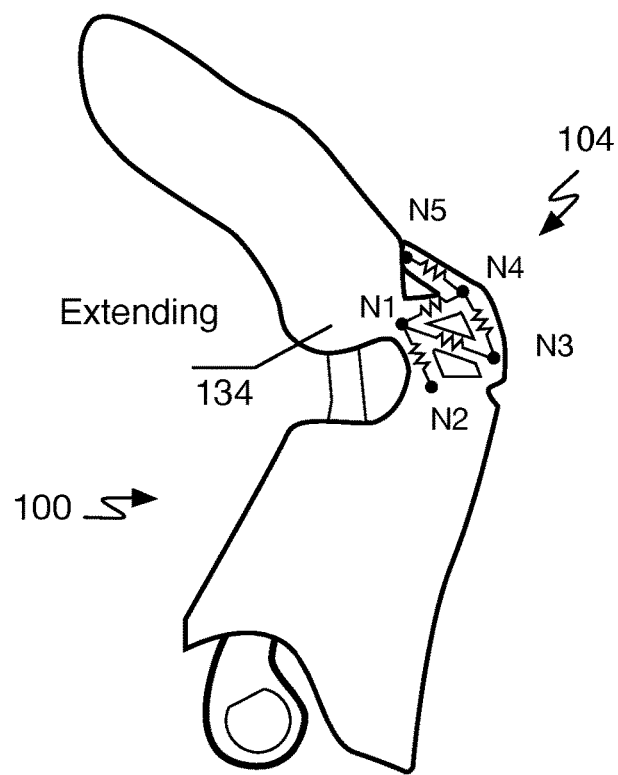

As shown in FIGS. 3A and 3B, a spring element model of a flexion force may be implemented about the PIP joint, with the flexion force being applied to the spring mesh at a point. The additional spring element during extension enables the variable stiffness of the compliant joint.

The compliant spring mesh structure is preferably defined by a network of structural springs in the sagittal plane. In one variation, a first portion of the structural spring mesh provides a first compliance factor within a first displacement range of the compliant joint, and when the compliant joint is displaced to a set position, a second portion of the structural spring mesh engages with the monolithic bone structure and provides a second compliance factor at positions beyond the set position.

More specifically, a first network of spring structures preferably engages at a first node Ni during flexion of the finger as shown FIG. 3A. The compliance factor of the structure of node Ni (e.g., the mesh structure form Node Ni to Node 2) in this mode provides the dominant force. Other areas of the compliant spring mesh such as nodes N3 and N4 may not be engaged or as significantly engaged. The node can be positioned at a central rotational position of the PIP joint. The first network of spring structures preferably has a first compliance factor. A second network of a spring structure is preferably defined in a different region and physically engages with a portion of the monolithic bone 100 when the monolithic bone 100 is actuated beyond a particular position. As shown in FIG. 3B, a distal segment of the monolithic bone 100 may physically engage a protruding sub-structure of the spring mesh structure at node N5. The compliance factor of the structure of node N5 (e.g., the mesh structure form Node N5 to Node 4) in this mode provides the dominant force. The sub-structure is preferably part of the second network of spring structures and has a compliance factor different from the first compliance factor. There may additionally be additional stages of compliance. For example, a third stage of compliance may be established by having a third network of spring structures that engage after engagement with the second network. In this variation, the finger may have a first stiffness initially when extending and then a second, greater stiffness after extending beyond a particular amount of deformation.

In other preferred variations, the compliant PIP joint may not have variable directional compliance. In these variations, either the spring mesh model is distributed such that the stiffness is equally distributed in all directions, or the compliant PIP joint utilizes one of the other compliant joint options discussed herein.

The monolithic bone 100 may be made of a single material but may alternatively include multiple material sub-components that are mechanically coupled into a monolithic structure. The monolithic bone structure is preferably made of a polymer-based material or any suitable type of compliant material.

In one preferred variation, the monolithic bone 100 is made of layers of nylon and thermoplastic polyurethane (TPU). The TPU functions to give the monolithic bone 100 flexibility and impact resistance. As a structural support, the monolithic bone 100 constructed of nylon and TPU layers may help reduce weight of the finger while enabling torsional flexural compliance as compared to the conventional four-bar linkage that is comprised of rigid links. The nylon functions to give the compliant bone stiffness and limit bending, particularly in the distal segment of the bone. The nylon and TPU components/layers may additionally be 3D-printed when producing the monolithic bone 100. Accordingly, the monolithic bone 100 can be partially constructed of three-dimensional printed components.

The monolithic bone 100 may alternatively be constructed of different materials. In some preferred variations, the monolithic bone 100 has an external nylon layer, a middle TPU layer, and an internal nylon layer. In preferred implementations, the internal nylon layer and the external nylon layer are disjointed at compliant joint sections. Additionally, the internal nylon layer is preferably not present within any compliant joint sections (e.g., the compliant PIP joint). In one variation, a nylon layer may be integrated into a rigid, non-actuating (and non-compliant) DIP segment extending from the output joint and/or the coupling link.

In some variations, the internal and external nylon layers are thin sheets (e.g., ~1.5 mm thick). In one example of these variations, the external nylon layer includes sheets comprising the sides of the monolithic bone (i.e., although curved, the sheets are along the sides of the monolithic bone that are roughly parallel to the plane of actuation of the monolithic bone). The sheets may travel along the entire length of the monolithic bone, although preferably disjointed at any compliant joint sections. Preferably, the nylon layers of a monolithic bone 100 are disjointed (i.e., not continuous) at the PIP joint. For example, there maybe a first nylon layer along the proximal phalanx region ending at the PIP joint (i.e., "below" the PIP joint) and a second nylon layer integrated in the monolithic bone structure above the PIP joint as part of the coupler link extending up to the output joint. In some preferred variations, the TPU material is monolithic or continuous through the monolithic bone 100 or part of the monolithic bone 100. For example, a region of TPU is preferably integrated into the monolithic bone 100 from the base up through the compliant PIP joint and to at least the output joint.

Figure 10:
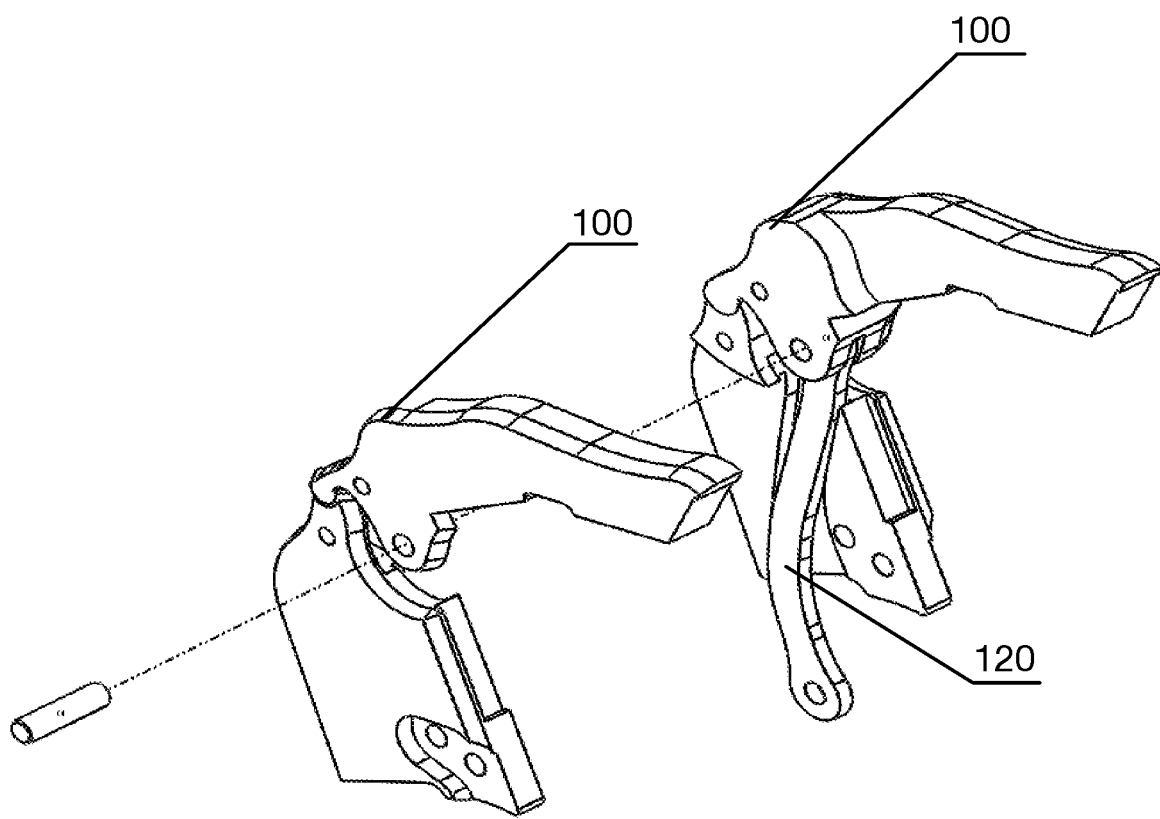
Figure 11:
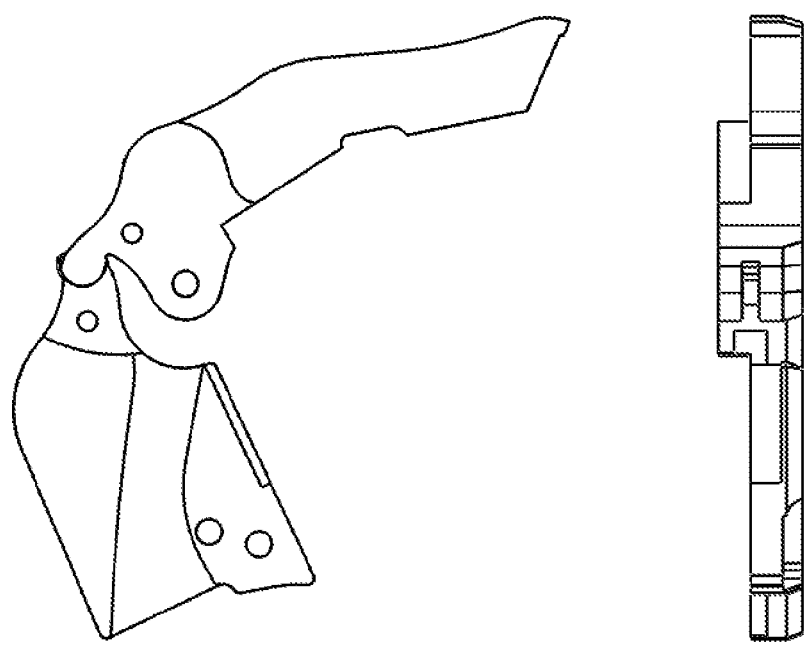
Figure 12:
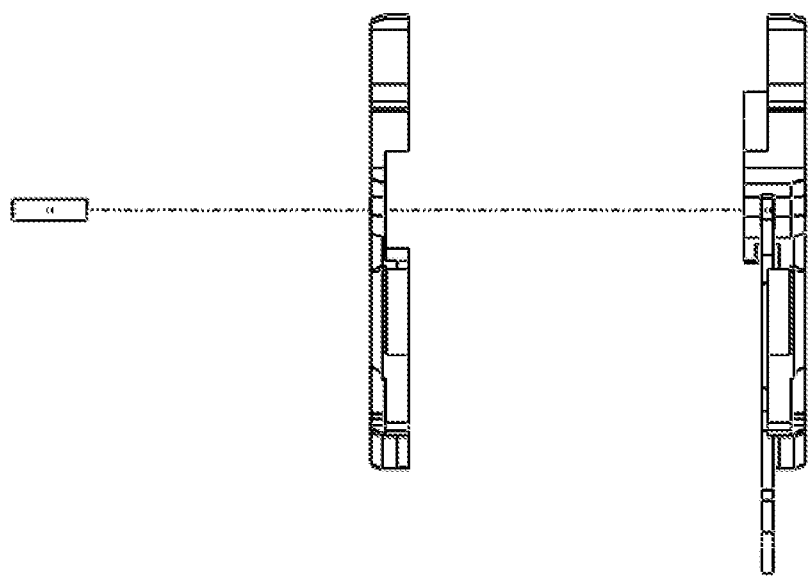

The monolithic bone maybe manufactured and assembled through a variety of techniques. As discussed, the monolithic bone 100 maybe 3D-printed in part or whole. The monolithic bone 100 may alternatively be injection molded, machined, and formed through any suitable manufacturing process. In one preferred implementation, a core structural component of the monolithic bone 100 is assembled from two monolithic bone halves that are attached together. The two monolithic bone halves are preferably split along the sagittal plane down the middle region of the resulting monolithic bone 100 as shown in FIGS. 10-12. The monolithic bone halves may not be identical halves, wherein one monolithic bone half may include additional components or features that are not included in, or on, the other monolithic bone half. Preferably the two halves are complimentary, with the first half entirely incorporating the compliant PIP joint and the second half physically coupling to the first half in a complimentary fashion; around the PIP joint or alternatively to one side of the PIP joint. The monolithic bone halves preferably connect along defined inside surfaces. The inside surfaces may have complimentary cavities to promote proper alignment. The inside surfaces may additionally couple in a configuration that defines an internal cavity. The internal cavity is preferably defined at least within the input link segment 103. In one variation, the output link 120 maybe assembled to at least partially be housed within the internal cavity, which can function to partially shield the output link 120.

Additionally, in some variation where the monolithic bone 100 is for a prosthetic limb, the monolithic bone 100 may include additional joints and structural features of the prosthetic limb. In one variation of a prosthetic finger, the monolithic bone 100 additionally includes a distal segment (i.e., a distal finger segment 106 in the finger use case) extending from the coupling segment 105 as shown in FIG. 2B. The distal segment is preferably an extension (or multiple extensions) beyond the DIP joint to a fingertip. In this example, the monolithic bone 100 may additionally include a preferred shape and size appropriate for the prosthetic finger (e.g., male ring finger, female index finger, etc.). In a preferred implementation, wherein the DIP joint is mechanically linked to the four-bar linkage section 102, the fingertip may function as a coupled end point to the four-bar linkage section 102.

The distal segment may optionally include distal interphalangeal (DIP) joint, which functions to simulate a DIP joint of a human hand. Accordingly, the distal segment can include two segments connected through a DIP joint. The DIP joint may be a compliant joint but may alternatively be a pivot joint, a fixed joint, or another type of joint. As a compliant joint, the DIP joint can use any suitable variation of a compliant joint discussed herein such as being a living hinge, a living spring, compliant mesh structure, and/or compliant material region. In another variation, the DIP joint could be actuated and may utilize a second compliant four-bar linkage mechanism for controlled actuation. But may alternatively use any suitable mechanism design. In another variation, the DIP joint is a fixed joint connecting the distal segment to the coupling segment.

In one example, the DIP joint is physically connected to the four-bar linkage section 102 of the monolithic bone 100 through the monolithic bone 100. In one variation, the DIP joint functions as a static segment extending from the main monolithic bone 100 to act as a structural fingertip/end effector. The DIP joint can be physically connected to the four-bar linkage section 102 of the monolithic bone 100 through the monolithic bone 100, but the DIP joint is not mechanically linked to the four-bar linkage section 102 and is fixed. During actuation of the four-bar linkage section 102, the DIP joint maintains a fixed position, thereby keeping the angle of the distal segment of the prosthetic finger fixed relative to its attachment point during finger actuation. In a preferred implementation, the DIP joint includes a nylon layer traversing the entire joint along the long axis of the finger to make the DIP joint additionally resistant to bending and bending forces. The additional resistance to bending may improve the gripping ability of the prosthetic hand.

In one variation, the DIP joint is compliant so as to flex or give at a DIP joint region or along the length of the segment. In an actuated DIP joint variation, actuation of the DIP joint is independent and not linked to the four-bar linkage section 102. In one implementation of this example, the DIP may have its own motor to provide a force for actuation. In a preferred example, the DIP joint may be mechanically linked to the four-bar linkage section 102 of the monolithic bone 100. Actuation of the four-bar linkage section 102 may then cause actuation of the DIP joint through stress and strain forces induced into the monolithic bone 100 by bending of the compliant joint and linkage components. In one preferred implementation, bending of the compliant PIP joint induces bending of the DIP joint. This bending may occur due to the flexion of the nylon layer of the monolithic bone 100 once the PIP joint bends.

In preferred variations, the monolithic bone 100 for a prosthetic finger may include an outer layer 107 as shown in FIG. 2C. Preferably, the monolithic bone 100 can be enveloped in a skin material. The skin material is preferably soft silicone skin, but other compounds (e.g., polymers/elastomers), or layers of compounds, may be alternatively used. The silicone skin functions to provide a protective layer for the internal mechanical components of the prosthetic finger and to provide a better surface for finger-environment interaction by the prosthesis. The soft silicone skin may increase the impact resistance of the prosthetic finger and prosthetic finger components. The soft material of the silicone skin has advantages in attenuation of impact forces, conformability, and repetitive strain dissipation. Additionally, the silicone skin may enable easier implementation of small components with the prosthetic finger (e.g., microchips). For example, in one preferred implementation, the silicone skin enables embedding a pressure-sensitive chip on the fingertip of the prosthetic finger.

The monolithic bone 100 may additionally include integrated sensors. In one variation, one or more sensors can be embedded in the fingertip (e.g., distal segment) of the prosthetic hand. The sensors may include a pressure sensor, light sensor, conductive sensor, or the like. In one variation, the monolithic bone 100 includes four MEMS barometric pressure sensors integrated into a defined cavity of the monolithic bone 100. In alternate variations, fewer or greater number of MEMS barometric pressure sensors or other types of sensors, may be integrated. Wires or conductive coupling to the sensors can preferably be channeled through defined cavities within the monolithic bone and/or outer layer. The barometric pressure sensors function to detect contact forces perpendicular to the fingertip surface. Other suitable sensors or active components may additionally or alternatively be integrated into the prosthetic finger.

The ground link 110 of a preferred embodiment functions as the fixed base structure during actuation of the compliant four-bar mechanism. The ground link 110 preferably connects to the monolithic bone 100 at one end and to the output link 120 at the opposite end at the drive joint 132 and the ground joint 136 respectively. The ground link 110 may be constructed of any desired material. In preferred variations for a prosthetic limb, the ground link 110 is the base structure that the prosthetic limb is connected to. For the preferred prosthetic finger example, the ground link 110 is part of the prosthetic hand that connects to the prosthetic finger. Preferably a palm body of the prosthetic hand serves as the ground link 110. In an implementation of a prosthetic hand, two or more prosthetic fingers can share a common ground link. For example, a palm body structure of a prosthetic hand may be used as a ground link for four or five fingers. In some variations, the prosthetic fingers may include a rotational degree of freedom for the thumb and/or other fingers wherein the ground link 110 may not be directly shared. In some embodiments the ground link 110 may not be a part of the system, wherein the prosthetic limb of the system is connected to an external ground link 110.

The output link 120 (also referred to as the follower link) of a preferred embodiment, functions as one of the actuating arms of the four-bar linkage. The output link 120 is preferably a distinct part from the monolithic bone 100. In configuring the four-bar linkage mechanism. The output link 120 preferably crosses paths of the input link segment 103 of the monolithic bone 100. In other words, the output link 120 preferably extends transverse to the input link segment 103. As discussed above, the monolithic bone structure can include a defined cavity, which is preferably defined within at least a portion of the input segment. The output link 120 can extend transverse to the input link segment 103 through the defined cavity.

The output link 120 is preferably made of a rigid material and in one variation the output link 120 is constructed of at least one layer of spring steel. In preferred variations, the output link 120 design enables it to be laterally compliant, but rigid in the flexion/extension direction to handle heavy loads. In one preferred variation, the output link 120 is a band or prismatic shape with two parallel "flat sides". This function to make the output link rigid in the direction of actuation but compliant to lateral forces.

Figure 13:
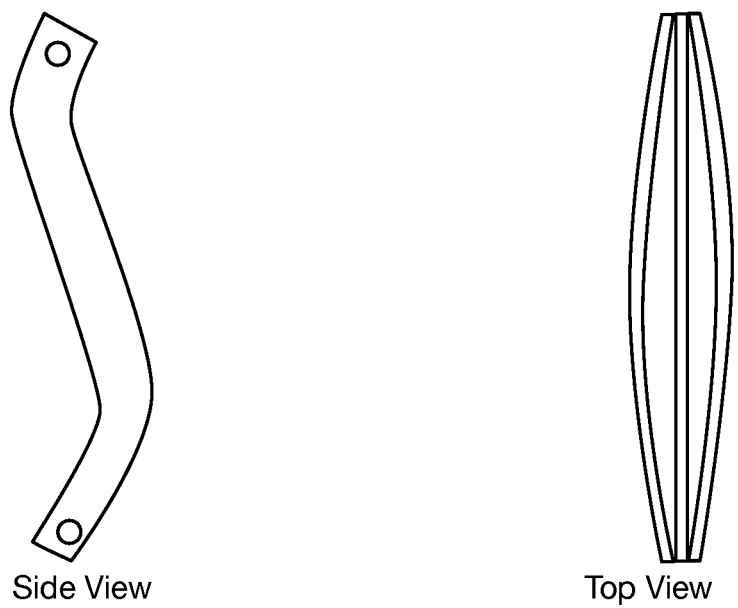
FIG. 13 is a side and top view of schematic representations of a variation of an output link.

In one variation, the output link 120 can be a laterally compliant multi-piece link. The multi-piece link preferably includes at least one outer link band and a central link band. The central link band is preferably straight along the sagittal plane. An outer link band is preferably curved or bowed so that it is not straight along the sagittal plane. The outer link band preferably has each end (proximal and distal) adjacent to the ends of the central link band and with a curvature form bowing outward from the sagittal plane between the two ends. More preferably, the multi-piece output link includes a central band of spring steel and two outer bands of spring steel, with the outer bands of spring steel forming a symmetric curvature about the central band. The two outer pieces of steel may be pre-stressed into different curvature forms, with the two outer pieces of steel displaced from a central piece of steel as shown in FIG. 13. Preferably, the two outer pieces of steel form a symmetric curvature about the central piece. Their curvature may alternatively not be symmetric if, for example, lateral compliance is configured to be different depending on the direction of the lateral force. The curved, outer pieces of steel may function to provide a strong lateral restorative force that enables the output link 120 to quickly recover to its initial state, restoring more energy upon impact. In another implementation, the output link 120 is constructed of a single piece of spring steel.

The joints of a preferred embodiment function to connect link components (e.g., ground link 110, output link 120, input link segment 103, and/or coupler link segment 105) and provide a locus for rotation of one connected linkage component with respect to the other connected linkage component. The system preferably comprises a set of at least three distinct joints; wherein a first joint—a drive joint 132 (or ground-input joint) connects the monolithic bone 100 to the ground link 110, the second joint—an output joint 134 (or output-coupler joint) connects the monolithic bone to the output link 120, and the third joint—ground joint 136 (or output-ground joint) connects the ground link 110 to the output link 120. Additionally, the system may include joints used in other mechanisms integrated into the prosthetic system or other suitable type of system.

Each joint may be of differing (or similar) construction and provide differences in actuation. In one variation, a joint maybe revolute pivot joint that provides a point of rotation between the two connecting linkage components. In one preferred implementation the revolute pivot joint is a pin joint. In another variation, a joint may be a compliant joint that provides a bending/deformation actuation for rotation. Preferably at least one of the joints is a compliant joint, but two, three, or four of the joints may additionally be compliant.

Figure 7:
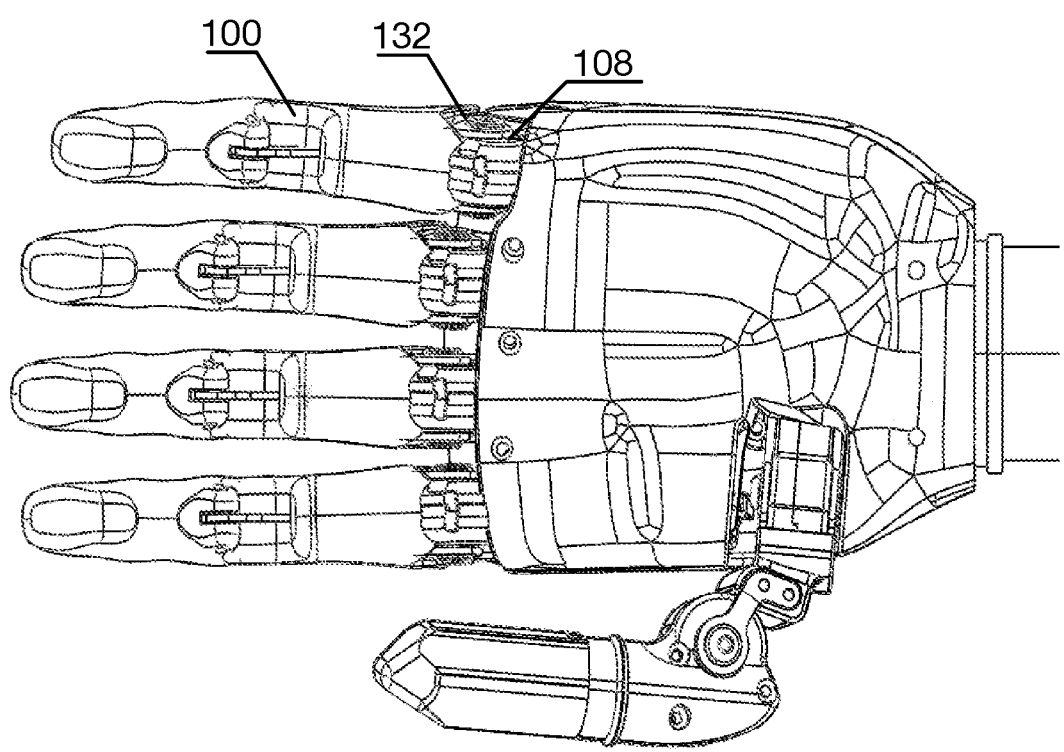
FIG. 7 is a schematic representation of a robotic hand of a preferred embodiment.
Figure 8:
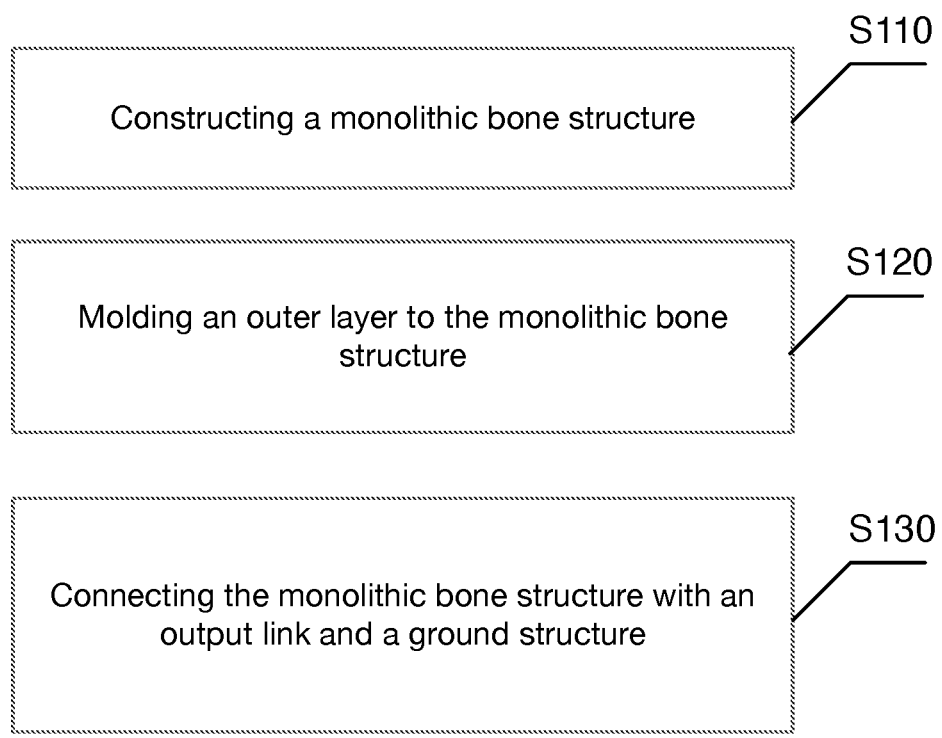
FIG. 8 is a flowchart of a method for fabrication of a prosthetic finger of a preferred embodiment.
Figure 9:
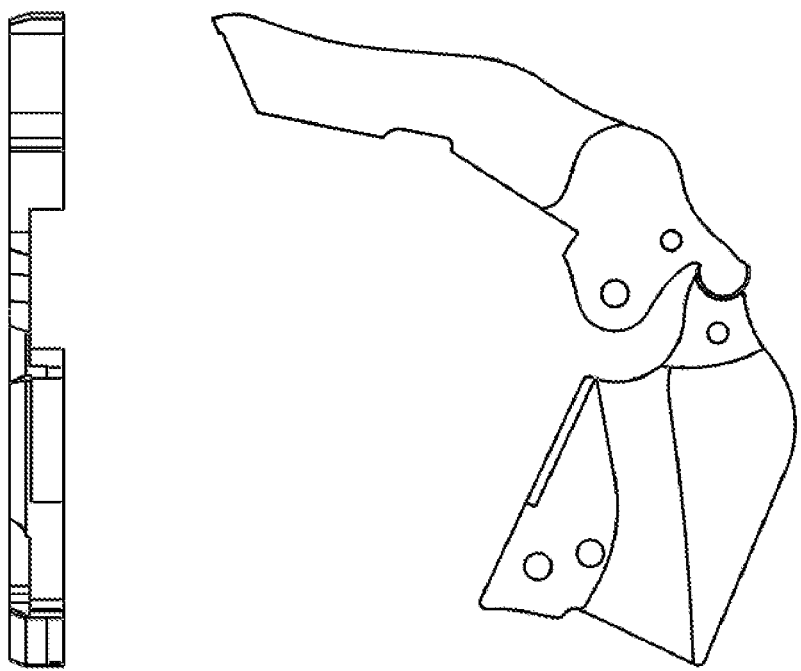
FIGS. 9-12 are schematic representations of parts of the monolithic bone.

The drive joint 132 of a preferred embodiment, as mentioned, functions to connect the monolithic bone 100 to the ground link 110. The drive joint 132 is preferably the actuated joint that drives actuation of the four-bar linkage mechanism. Preferably, the drive joint 132 is coupled to an actuation input system 140. In one preferred implementation, the drive joint 132 is mechanically coupled to worm gear that is controlled by a motor. The worm gear mechanism is preferably mechanically coupled to the input joint as shown in FIG. 7. Other joints may alternatively serve as the actuated joint such as in alternative applications.

In the preferred example of a prosthetic finger, the drive joint 132 can function as a metacarpophalangeal (MCP) joint within the finger prosthesis. The MCP joint preferably connects the prosthetic finger body (i.e., monolithic bone 100) to the prosthetic hand (i.e., ground link 110). In one variation, the MCP joint is a compliant pivot joint, but may alternatively be a pivot joint or a compliant joint. The MCP compliant joint may in some variations be configured into a torsionally compliant metacarpophalangeal input joint.

The output joint 134 of a preferred embodiment, as mentioned, functions to connect the monolithic bone 100 to the output link 120. The output joint 134 is preferably a pivot joint but may be an alternative type of joint.

The ground joint 136 of a preferred embodiment, as mentioned, functions to connect the ground link 110 to the output link 120. As part of a four-bar linkage, the ground joint 136 may additionally be referred to as a ground joint. For the preferred example of a prosthetic finger, the ground joint 136 connects the prosthetic hand (i.e., ground link 110) to the follower link (i.e., output link 120). The ground joint 136 is preferably a pivot joint but may be an alternative type of joint.

In preferred variations, parameters for the links of the four-bar linkage mechanism are designed to satisfy the double-crank Grashof condition. In this example, the length of input link section of the monolithic bone 110 is AB, the length of floating section of the monolithic bone 100 is BC, the length of the ground link 110 is AD, and the length of the output link 120 is CD. The double-crank Grashof condition is met when:

$$T_1 = AD + BC - AB - CD < 0,$$

$$T_2 = CD + AD - AB - BC < 0,$$

$$T_3 = CD + BC - AB - AD > 0.$$

The four-bar linkage mechanism is preferably an inverted double-crank mechanism but may alternatively not be inverted. We define the coupling lengths from compliant joint 104 (i.e., the PIP joint) of the monolithic bone 100 to the fingertip as CE and from the output joint 134 to the fingertip as BE. In one preferred implementation: AD=8.55 mm, AB=37.11 mm, BC=8.78 mm, CD=37.04 mm, CE=32.77 mm, and BE=40.38 mm. Additionally, the range of motion is 105.0° for the drive joint 132 (i.e., MCP joint) and 93.0° for the compliant joint 104. With respect to the drive joint 132, the range of motion of the fingertip is 154.4° when no load is applied. The range of motion of alternative implementations may be greater or less than these exemplary ranges.

Figure 4:
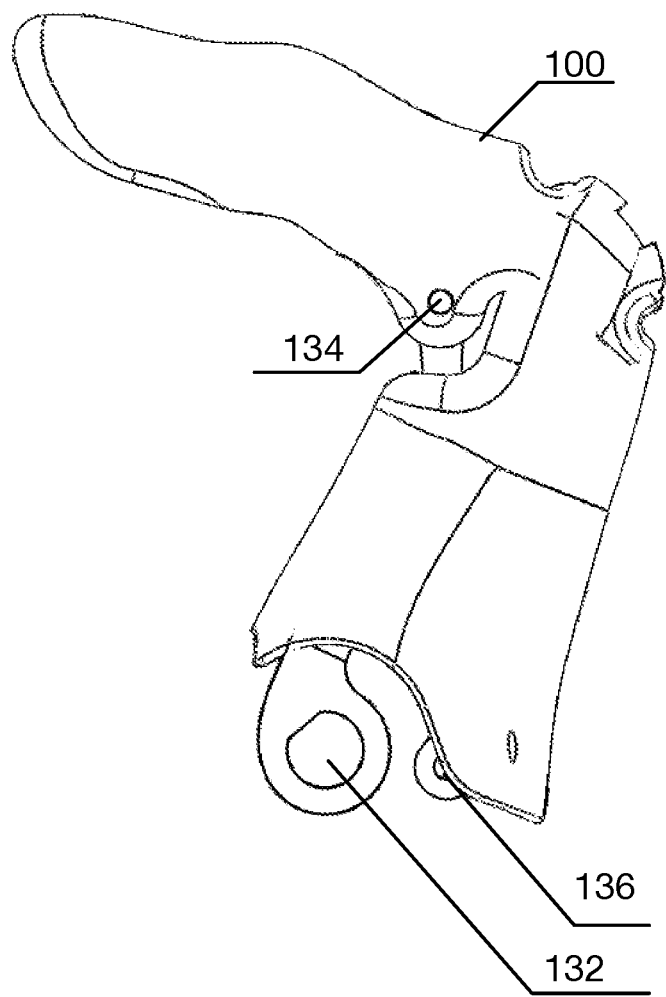
FIGS. 4-6 are schematic representations of the robotic finger assembly.
Figure 5:
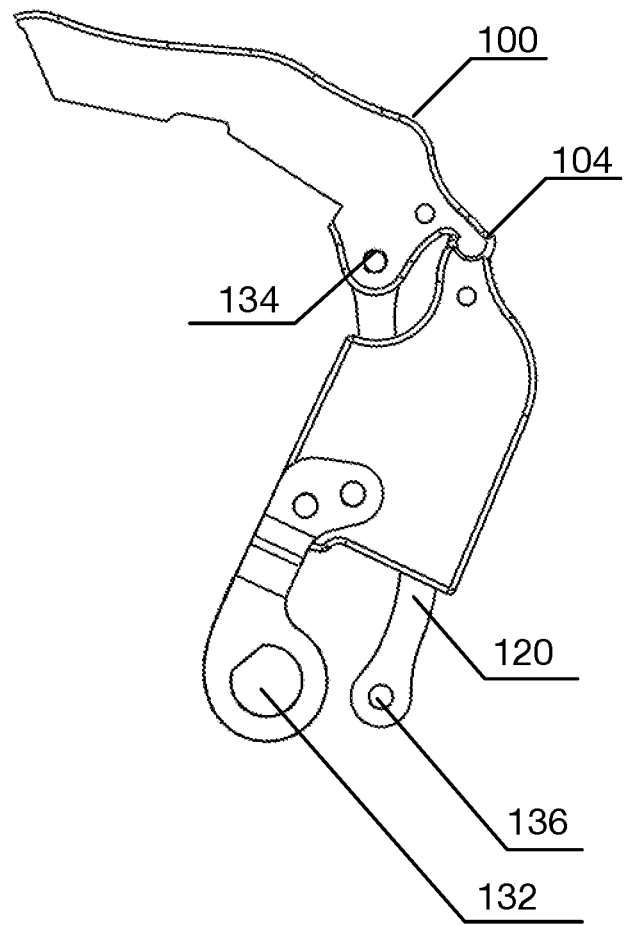
Figure 6:
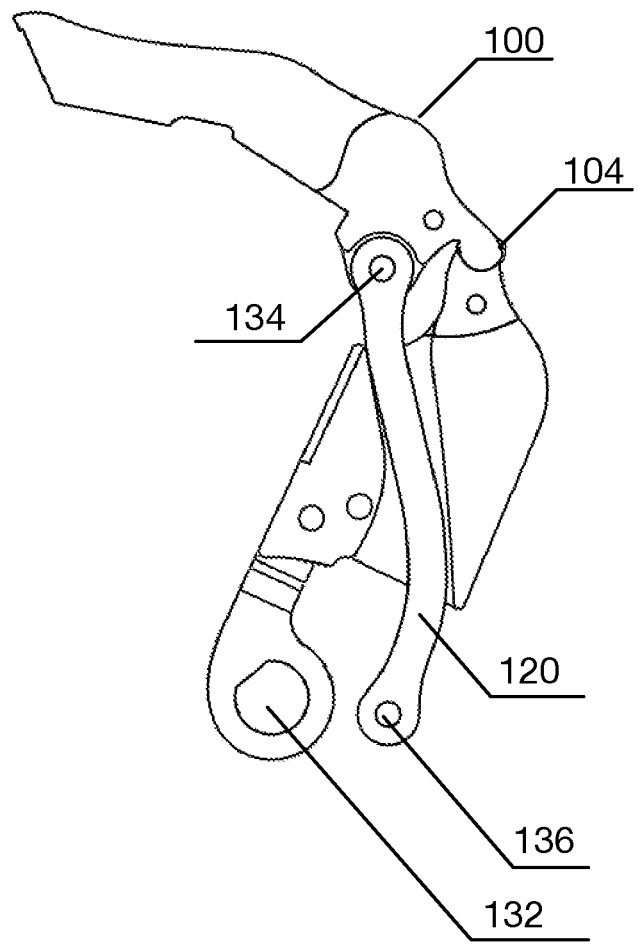

As discussed, the prosthetic finger maybe integrated into a prosthetic hand as shown in FIG. 7. The prosthetic hand preferably has a plurality of compliant 4-bar linkage driven prosthetic fingers. FIGS. 4-6 show different layers of one prosthetic finger of preferred embodiment for the prosthetic hand. The hand has six degrees of freedom corresponding to the flexion/extension mechanism of the compliant 4-bar linkage mechanism for each finger, excluding the thumb, with additional actuation mechanisms for two degrees of freedom for a thumb prosthetic finger. Preferably, the additional degrees of freedom in the thumb are rotational actuation for opposition and/or flexor actuation. In one implementation, the system may additionally include six DC brushless motors each mated to a single-envelope worm transmission drive for each degree of freedom. In an alternative implementation, the system may additionally include a motor for each compliant 4-bar linkage mechanism. In one variation, six 100:1 HPCB Pololu Micro Metal Gearmotors each mated to a single-envelope worm transmission drive for each degree of freedom can be used. Worm gears may function to make each finger nonbackdrivable for energy efficiency. A user with upper limb amputations may control the prosthetic hand using electromyographic pattern recognition. The user may additionally receive feedback by receiving contact pressure through vibrotactile or electrotactile sensory substitution transduced from the fingertip pressure sensors.

3. Method

As shown in FIG. 7, fabricating a prosthesis with an integrated compliant four-bar linkage mechanism of a preferred embodiment can include constructing a monolithic bone structure S110, molding an outer layer to the monolithic bone structure S120, connecting the monolithic bone structure with an output link and a ground structure S130. The method preferably functions to fabricate the prosthetic finger as described above as part of a compliant four-bar linkage mechanism but may be implemented in fabricating a compliant finger bone for other purposes. The method preferably includes processes directed at building a four-bar linkage mechanism and a prosthesis substantially similar to the one described above. The method may additionally be extended to fabrication of a set of compliant finger prostheses that are assembled as part of another system such as a prosthetic hand.

Block S110, which includes constructing a monolithic bone structure, functions to fabricate the main support body of the prosthetic finger. The resulting monolithic bone structure is preferably substantially similar to the one described in the system above. Accordingly, constructing a monolithic bone structure can include forming a monolithic bone structure comprised of an integrated structure that includes a first segment (e.g., an input link segment) and a second segment (e.g., a coupler link segment) compliantly coupled through a compliant joint. Additionally, constructing a monolithic bone structure can include forming a distal segment, which may additionally include forming a distal segment with an additional joint, which could function as a DIP joint of a prosthetic fingertip.

Constructing a monolithic bone structure can include constructing at least a compliant joint with a compliant material. A compliant material is preferably a polymer. More specifically, the compliant material is made of a flexible thermoplastic polyurethane but may alternatively be any suitable material. The compliant joint may be printed or manufactured so as to partially or fully be in a flexed resting state; that is the resting state of the system may hold or maintain the compliant joint in a flexed position state. Manufacturing the compliant joint in a flexed resting state functions to promote a natural tendency of the hand to be in flexion. This may give the prosthetic finger added torque when flexing (versus extending) making the grip stronger. A flexed resting state may be a structural configuration of where the angle of the PIP joint is at an angle closer to a minimum angle (e.g., the angle when flexing/gripping) than a maximum angle (e.g., the angle when fully extended/open finger position).

In one variation, constructing the monolithic bone structure Sino preferably includes 3D-printing the monolithic bone structure. In one preferred variation, constructing a monolithic bone structure Sino more specifically includes 3D-printing multiple subcomponents and assembling the monolithic bone structure into a single body. In a preferred example, building the monolithic bone structure Sino includes printing the monolithic bone in two parts, and then gluing the two parts of the monolithic bone together. FIGS. 9-12 show the two separate parts of the monolithic bone. Alternatively, the two parts can be fastened together (e.g., screwed together, latched together, annealed together) or connected in any suitable manner. Preferably the two parts include complimentary surfaces that in some regions mate together to form a continuous form and in other regions define functional cavities. Preferably, the monolithic bone structure includes an internal defined cavity, which can be used to house the output link when assembled. The defined internal cavity preferably allows for the range of motion of the output link.

In one preferred implementation, 3D-printing the monolithic bone is accomplished using a MakerGear M2 printer, although another 3D printer may be implemented. The monolithic bone is preferably constructed of flexible thermoplastic polyurethane (Cheetah, NinjaTek) and nylon (Alloy 910, Taulman3D) filaments, but any suitable material maybe used.

In some preferred variations, constructing a monolithic bone Sino may further include embedding sensors into the prosthetic finger. In these preferred variations, the method further includes 3D-printing a distal fingertip structure and embedding sensors into the tip of the distal fingertip structure. In one preferred example, four MEMS barometric pressure sensors are embedded into the tip of the distal fingertip bone. The four MEMS barometric pressure sensors function to detect contact forces perpendicular to the fingertip surface. To detect contact forces, the sensing hole of the pressure sensor is filled with silicone or other suitable materials. Building the monolithic bone then further includes inserting and annealing the pressure sensors to the distal fingertip bone section of the monolithic bone, with the pressure sensors between the two 3D-printed monolithic bone parts. Additional or alternative sensors may alternatively be integrated when constructing the monolithic bone S110.

Block S120, which includes molding an outer layer to the monolithic bone structure, functions in covering the monolithic bone in a soft "skin" layer. In one preferred implementation the outer layer is a silicone skin that is overmolded onto monolithic bone structure. The silicone skin may additionally function in protecting internal components of the prosthetic finger. Molding an outer layer to the monolithic bone structure preferably includes setting the monolithic bone structure into a mold, casting the outer layer material into the mold, and removing a coated monolithic bone structure from the mold. When setting the monolithic bone structure into the mold various inserts such as two shafts inserted into the joint couplers of the monolithic bone structure to prevent the outer layer from filling those cavities. Once the outer layer cures, the outer layer preferably closely lines the monolithic bone at least in some regions. In some variations, the molded outer layer may form one or more structural elements of the resulting coated monolithic bone structure. For example, the prosthetic fingertip may be partially formed from the outer layer material. The outer layer material may additionally work in coordination with the monolithic bone structure to provide the desired dynamics of a compliant joint.

After fabrication of the prosthetic finger, the method may further include cutting a hole in the silicone skin over the connecting joints, thus enabling connection of additional links in creating a compliant 4-bar linkage mechanism as previously described in the system.

Block S130, which includes connecting the monolithic bone structure with an output link and a ground structure, functions to assemble the components of the compliant four-bar linkage mechanism. Connecting the monolithic bone structure with the output link and ground structure preferably includes inserting an output link into position with the monolithic bone structure, coupling the output link on a first end to an output joint coupler of the monolithic bone structure, and coupling the output link on a second end to a ground joint, and attaching an actuation system to an input joint coupler of the monolithic bone structure. The ground joint and the input joint coupler are preferably coupled through the ground link, which in a preferred implementation is part of the base of a prosthetic hand (e.g., a palm). In one preferred implementation, attaching an actuation system to an input joint coupler preferably includes engaging a worm gear mechanism to the input joint coupler. The worm gear mechanism is preferably driven by a mechanically coupled motor.

In some preferred variations, connecting the bone structure with an output link and a ground structure S130 includes connecting the structures such that the monolithic bone structure is initially in a partially, or fully, pre-flexed state, i.e., a flexed resting state as discussed above. The flexed resting state of the monolithic bone structure may function to give the prosthetic finger added torque when flexing (vs. extending).

Repeating of blocks S110, S120, and S130 may be implemented in assembling a multi-finger prosthesis.

As a person skilled in the art will recognize from the previous detailed description and from the figures and claims, modifications and changes can be made to the embodiments of the invention without departing from the scope of this invention as defined in the following claims.

We claim:

1. A system for a prosthetic finger comprising:
 a monolithic bone structure comprised of a compliant joint region and an input link segment and a coupler link segment, wherein the input link segment and the coupler link segment are connected through the compliant joint region, wherein the compliant joint region is made of a compliant material;
 an output link;
 a ground structure;
 wherein the monolithic bone structure, output link, and ground structure are connected through a set of joints in a configuration of a compliant four-bar linkage mechanism which comprises of:

the output link on a first end and the coupler link segment connected through an output joint, the output link on a second end connected to a ground joint on the ground structure, and the monolithic bone structure connected to an input joint connected to the ground structure; and an actuation input coupled to the input joint.

2. The system of claim 1, wherein the output link extends transverse to the input link segment of the monolithic segment.

3. The system of claim 2, wherein the monolithic bone structure comprises a defined cavity within at least a portion of the input segment; and wherein the output link extends transverse to the first input link segment through the defined cavity.

4. The system of claim 1, further comprising an outer layer molded onto the monolithic bone structure.

5. The system of claim 1, wherein the actuation input comprises a worm gear mechanism that is mechanically coupled to the input joint and a motor that drives the worm gear mechanism.

6. The system of claim 1, wherein the input joint and the ground joint are displaced by at least 8.5 millimeters; wherein the input segment has a length of at least 37 millimeters; wherein the coupler link segment has a length of at least 8.7 millimeters, and the output link has a length of at least 37 millimeters.

7. The system of claim 1, wherein the ground structure provides the base of actuation for the compliant four-bar linkage mechanism and is part of a prosthetic hand.

8. The system of claim 1, wherein the monolithic bone structure is partially constructed of three-dimensional printed components.

9. The system of claim 1, wherein the monolithic bone structure is made of a polymer-based material.

10. The system of claim 1, wherein the monolithic bone structure further comprises a distal finger segment extending from the coupler link segment.

11. The system of claim 10, wherein the distal finger segment comprises a compliant distal interphalangeal joint.

12. The system of claim 1, wherein the compliant joint region is structurally configured with a first compliance factor within a first displacement range and a second compliance factor within a second displacement range.

13. The system of claim 1, wherein the compliant joint region comprises a structural spring mesh, wherein a first portion of the structural spring mesh provide a first compliance factor within a first displacement range of the compliant joint region, and when the compliant joint region is displaced to a set position, a second portion of the structural spring mesh engages with the monolithic bone structure and provides a second compliance factor at positions beyond the set position.

14. The system of claim 1, wherein the output link is comprised of a central band of spring steel and two outer bands of spring steel, with the outer bands of spring steel forming a symmetric curvature about the central band.

15. A system for a prosthetic finger comprising:

a monolithic bone structure comprised of a compliant proximal interphalangeal joint and an input link segment and a coupler link segment, wherein the input link segment and the coupler link segment are connected through the compliant proximal interphalangeal joint, wherein the compliant proximal interphalangeal joint is made of a compliant material;

an output link;

a prosthetic hand structure;

wherein the monolithic bone structure, output link, and a prosthetic hand structure are connected through a set of joints in a configuration of a compliant four-bar linkage mechanism which comprises of:

the output link on a first end and the coupler link segment connected through an output joint, the output link on a second end connected to a ground joint on the prosthetic hand structure, and the monolithic bone structure connected to a metacarpophalangeal input joint connected to the prosthetic hand structure; and an actuation input coupled to the compliant metacarpophalangeal input joint.

16. The system of claim 15, wherein the monolithic bone structure further comprises a fingertip section extending from the coupler link segment, the fingertip section including two segments connected through a distal interphalangeal joint.

17. A system for a prosthetic hand comprising:

a base palm body with a set of worm gear actuation systems integrated into the base palm body;

a set of compliant four-bar linkage mechanisms configured as prosthetic fingers, wherein each four-bar linkage mechanism comprises:

a monolithic bone structure comprised of a compliant joint region and an input link segment and a coupler link segment, wherein the input link segment and the coupler link segment are connected through the compliant joint region, wherein the compliant joint region is made of a compliant material;

an output link;

wherein the output link on a first end and the coupler link segment are connected through an output joint, the output link on a second end is connected to a ground joint on the base palm body, and the monolithic bone structure is connected to an input joint connected to the base palm body; and wherein the worm gear actuation system mechanically couples to the input joint;

wherein each four-bar linkage mechanism engages with one worm gear actuation system of the set of worm gear actuation systems at an input joint of each four-bar linkage mechanism.

18. The system of claim 17, further comprising an outer layer molded onto the monolithic bone structure.

19. The system of claim 17, wherein the monolithic bone structure further comprises of a fingertip section extending from the coupler link segment, the fingertip section including two segments connected through a compliant distal interphalangeal joint.

20. The system of claim 17, wherein the input joint is a torsionally compliant metacarpophalangeal input joint.

* * * * *